US00PP09687P

United States Patent [19]

Olesen et al.

[11] Patent Number: Plant 9,687

[45] Date of Patent: Nov. 12, 1996

[54] MINIATURE ROSE PLANT NAMED 'POULROUGE'

[75] Inventors: Mogens N. Olesen; Pernille Olesen, both of Fredensborg, Denmark

[73] Assignee: Bear Creek Gardens, Inc., Medford, Oreg.

[21] Appl. No.: 588,053

[22] Filed: Jan. 19, 1996

[51] Int. Cl.[6] ..... A01H 5/00

[52] U.S. Cl. ..... Plt./10

[58] Field of Search ..... Plt./7.1, 10, 10.1

*Primary Examiner*—Howard J. Locker

*Attorney, Agent, or Firm*—Klarquist Sparkman Campbell Leigh & Whinston, LLP

[57] ABSTRACT

A miniature rose plant having a compact vigorous growth habit suitable for pot rose production, producing long lived, bright orange flowers and easily reproduced from soft wood cuttings, the plants being forcible into flower in 14 weeks.

1 Drawing Sheet

The present invention relates to a new and distinct variety of rose plant of the miniature class which was originated by our crossing the variety POULion, not patented, with an unnamed seedling.

The primary objective of this breeding was to produce a new rose variety having the compact habit, ease of rooting and rapid growth of the female parent POULion combined with the bright orange flower color, hard petals and larger flowers of the unnamed seedling male parent. The objective was substantially achieved, along with other desirable improvements, as evidenced by the following unique combination of characteristics that are outstanding in the new variety and that distinguish it from its parents, as well as from all other varieties of which we are aware:

1. Compact vigorous growth habit suitable for miniature pot rose production under greenhouse conditions;
2. Bright orange flowers that fade very little;
3. Long lived flowers;
4. Ease of rooting as softwood cuttings; and
5. Plants from cuttings can be forced into flower in 14 weeks.

Asexual reproduction of this new variety by softwood cuttings, as performed at Somis, Calif., and Fredensborg, Denmark, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of our new rose cultivar with color descriptions using terminology in accordance with The Royal Horticultural Society (London) Colour Chart, except where ordinary dictionary significance of color is indicated.

Parentage:

*Seed parent.*—POULion.

*Pollen parent.*—Unnamed seedling.

Classification:

*Botanical.*—Rosa hybrida.

*Commercial.*—Miniature.

FLOWER

Observations made from specimens grown in a greenhouse environment in Somis, Calif., January through November, 1995.

Blooming habit: Continuous.

Bud:

*Size.*—½ inch to ⅝ inches long when the petals start to unfurl.

*Form.*—Short, pointed ovoid.

*Color.*—When sepals first divide, bud color is Red Group 40B. When half blown, the upper sides of the petals are Red Group 40B; and the lower sides of the petals are Red Group 41B.

*Sepals.*—Color: Green Group 138B. Surface texture: Covered in many fine hairs. There are three lightly appendaged sepals. There are two unappendaged sepals with hairy edges.

*Receptacle.*—Color: Green Group 137C. Shape: Apple. Size: Small (⅛"×⅛"). Surface: Smooth.

*Peduncle.*—Length: Short (1¼"). Surface: Glandular. Color: Medium green. Strength: Stiff, erect, slender.

Bloom:

*Size.*—Small. Average open size is 1½ inches.

Borne.—Singly and several together in flat clusters.

*Stems.*—Short, strong. Average length is about 4 to 6 inches.

*Form.*—When first open: High center. Permanence: Flattens, outer petals curl back.

Petalage.—Number of petals under normal conditions: 30 to 35.

*Color.*—The upper side of each petal is Red Group 40B. The reverse side of each petal is Red Group 41B. The base of each petal has a small (3/16"×3/16") light yellow half moon at the point of attachment of color Yellow Group 7D. The major color on the upper side is Red Group 40B.

*Variegations.*—Occasional white streak on the guard petals.

*Discoloration.*—No general tonality at the end of the first day and for several days thereafter. By day 5 or 6, there is a general fading to Red Group 40C.

*Fragrance.*—None.

Petals:

*Texture.*—Thick, leathery.

*Shape.*—Round to slightly deltoid.

*Form.*—Tips slightly recurved.

*Arrangement.*—Imbricated, with few petaloids in the center.

*Persistence.*—Drop off cleanly.

*Lastingness.*—On the plant: Long, 7 to 8 days. As a cut flower: Long, 8 to 10 days.

Reproductive parts:

*Anthers.*—Size: Small. Quantity: Many. Color: Yellow. Arrangement: Regular around styles, mixed with occasional petaloids.

*Filaments.*—Color: Yellow.

*Pollen.*—Color: Lemon yellow.

*Styles.*—Color: Greenish white.

Stigmas.—Color: Greenish white.

Form: Bush.

Growth: Vigorous; dwarf; upright; branching; compact. When grown in a 5-inch pot, the plant is 10 inches to 12 inches tall (above soil line) and 6 inches to 8 inches wide.

Foliage:

*Size.*—Small (2½"×2").

*Quantity.*—Abundant.

*Color.*—New foliage: Very little anthocyanin content in upper surface. Upper: Green Group 137A. Lower: Greyed Red 178A. Quickly turns green. Old foliage: Upper: Green Group 136A. Lower: Green Group 136C.

Leaflets:

*Number.*—5 or 7 on normal mid-stem leaves.

*Shape.*—Pointed oval.

*Texture.*—Upper side: Glossy, smooth.

*Edge.*—Serrated.

*Serration.*—Single, small.

*Petiole rachis color.*—Green with some anthocyanin pigment on young leaves.

*Petiole underside.*—Smooth with occasional prickles.

*Stipules.*—Short, bearded.

*Disease resistance.*—Susceptible to mildew under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Short, straight.

*Color when young.*—Green.

Small prickles:

*Quantity.*—On main stalks: None. On laterals: None.

We claim:

1. A new and distinct variety of rose plant of the miniature class, substantially as herein shown and described, characterized particularly as to novelty by the unique combination of its compact but vigorous growth; its bright orange flower color; its long lived flowers; and its ease of rooting when produced from softwood cuttings.

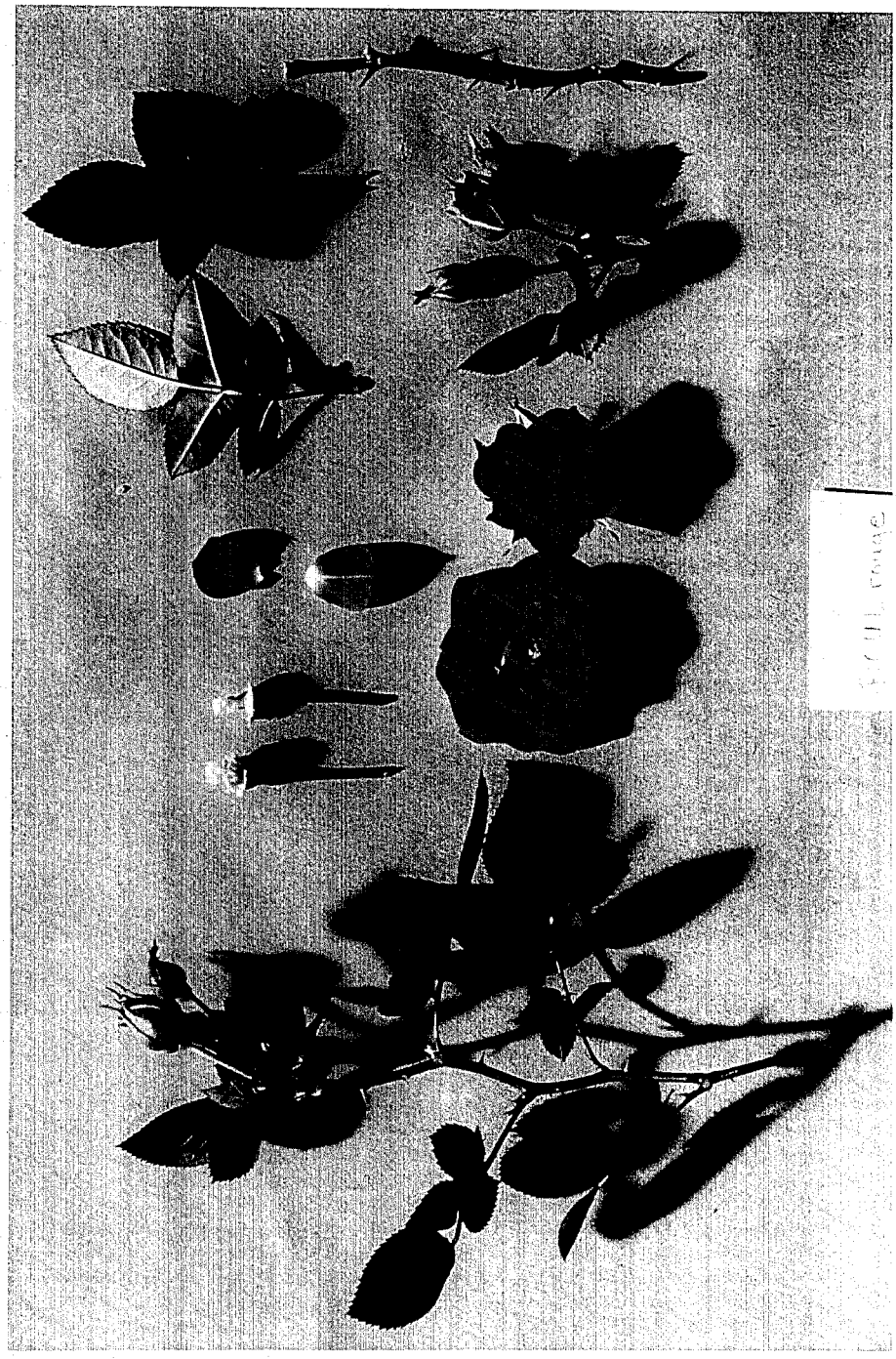

* * * * *